(12) United States Patent
Popowski et al.

(10) Patent No.: US 8,617,117 B2
(45) Date of Patent: Dec. 31, 2013

(54) MEDICAL TUBING ASSEMBLY TO FACILITATE TUBE FIXATION

(75) Inventors: Youri Popowski, Genève (CH); Erwin Berger, Stettfurt (CH)

(73) Assignee: Acrostak Corp., Winterthur (CH)

( * ) Notice: Subject to any disclaimer, the term of this patent is extended or adjusted under 35 U.S.C. 154(b) by 446 days.

(21) Appl. No.: 12/998,223

(22) PCT Filed: Oct. 8, 2009

(86) PCT No.: PCT/EP2009/063111
§ 371 (c)(1),
(2), (4) Date: Mar. 28, 2011

(87) PCT Pub. No.: WO2010/040811
PCT Pub. Date: Apr. 15, 2010

(65) Prior Publication Data
US 2011/0213308 A1 Sep. 1, 2011

Related U.S. Application Data

(60) Provisional application No. 61/103,662, filed on Oct. 8, 2008.

(30) Foreign Application Priority Data

Oct. 8, 2008 (EP) .................................... 08166060

(51) Int. Cl.
*A61M 25/04* (2006.01)
*F16L 21/00* (2006.01)
*F16L 15/00* (2006.01)

(52) U.S. Cl.
USPC .............................. 604/175; 285/399; 285/300

(58) Field of Classification Search
USPC ................. 604/175, 533, 523, 524, 534, 535; 285/399, 390
See application file for complete search history.

(56) References Cited

U.S. PATENT DOCUMENTS

| 909,344 | A | * | 1/1909 | Stratton | 285/22 |
| 5,105,807 | A | | 4/1992 | Kahn et al. | |
| 5,728,061 | A | * | 3/1998 | Ahmed | 604/9 |
| 5,743,869 | A | * | 4/1998 | Ahmed | 604/9 |
| 6,200,294 | B1 | * | 3/2001 | Liu | 604/198 |
| 6,558,349 | B1 | | 5/2003 | Kirkman | |
| 2007/0151889 | A1 | * | 7/2007 | Brady | 206/509 |

FOREIGN PATENT DOCUMENTS

EP    1 731 190 A1    12/2006

OTHER PUBLICATIONS

The International Search Report for PCT Application No. PCT/EP2009/063111.

* cited by examiner

*Primary Examiner* — Emily Schmidt
*Assistant Examiner* — Michael J Anderson
(74) *Attorney, Agent, or Firm* — Amster, Rothstein & Ebenstein LLP

(57) ABSTRACT

The invention concerns a medical tubing assembly (100) comprising: finned medical tubing (10) formed from an elongate tubular member (20) disposed with one or more longitudinal fins (21, 21', 21"), a collar (200), slidably mountable on the finned tubing (10), equipped with a locking means and optionally one or more suture eyelets (250, 250'), said locking means configured to provide a locking force against one or more of the longitudinal fins (21, 21', 21"). The invention allows securing of a medical tubing in situ that prevents slippage or damage to the tubing wall.

19 Claims, 13 Drawing Sheets

Figure 1:
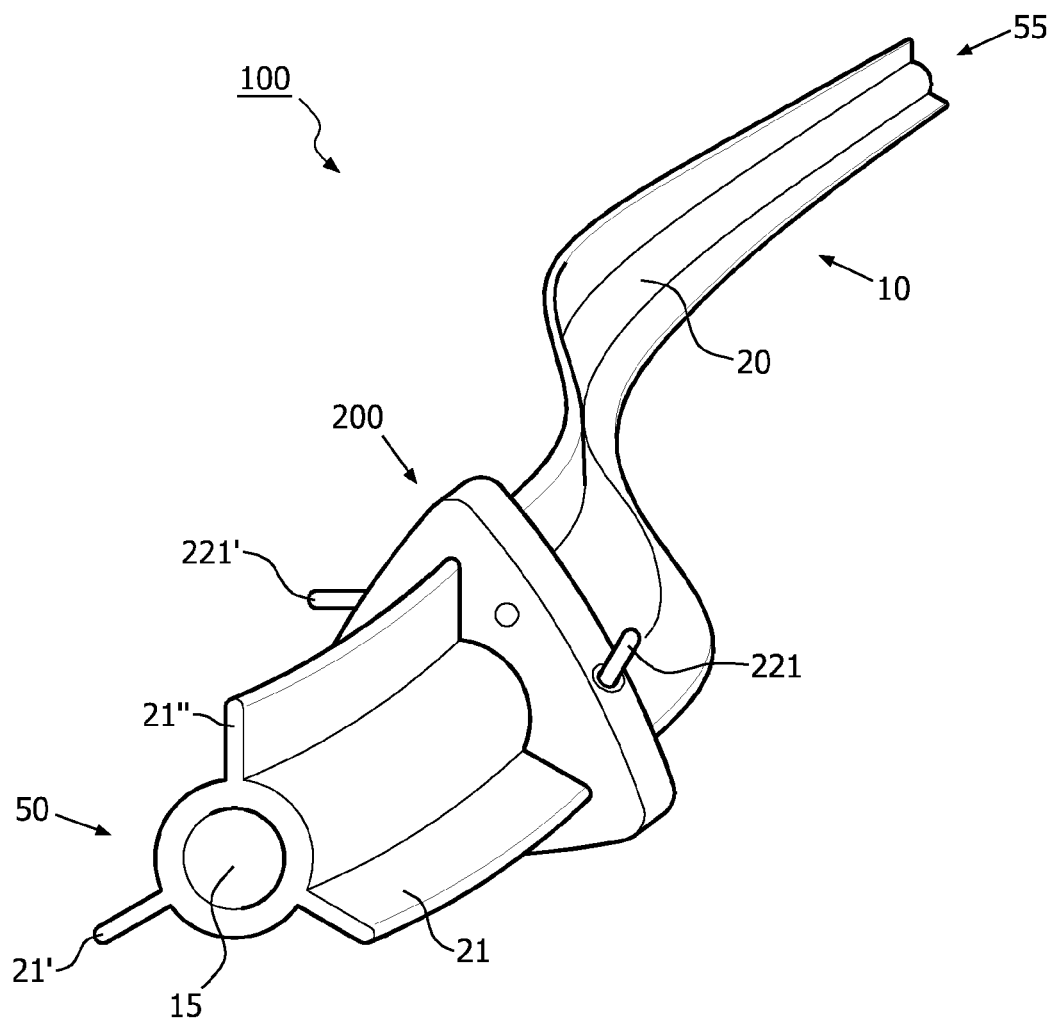

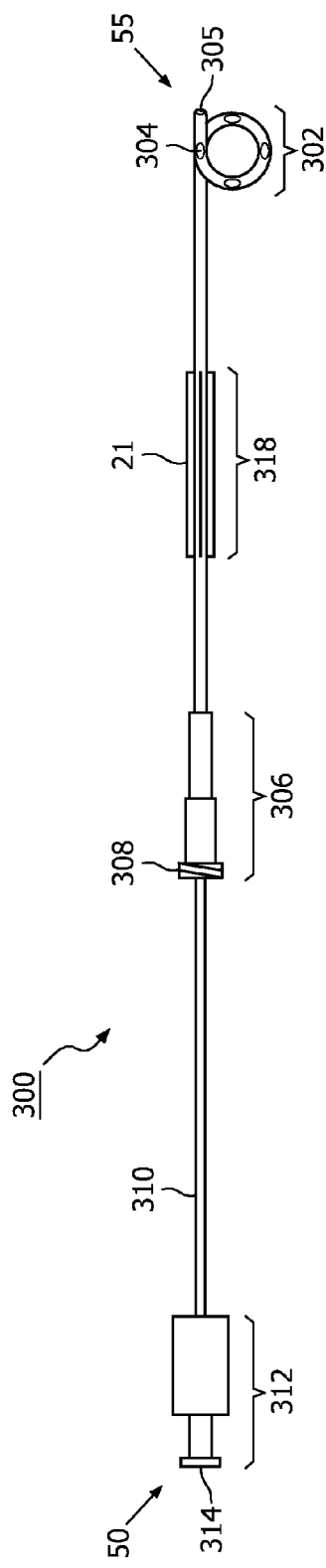
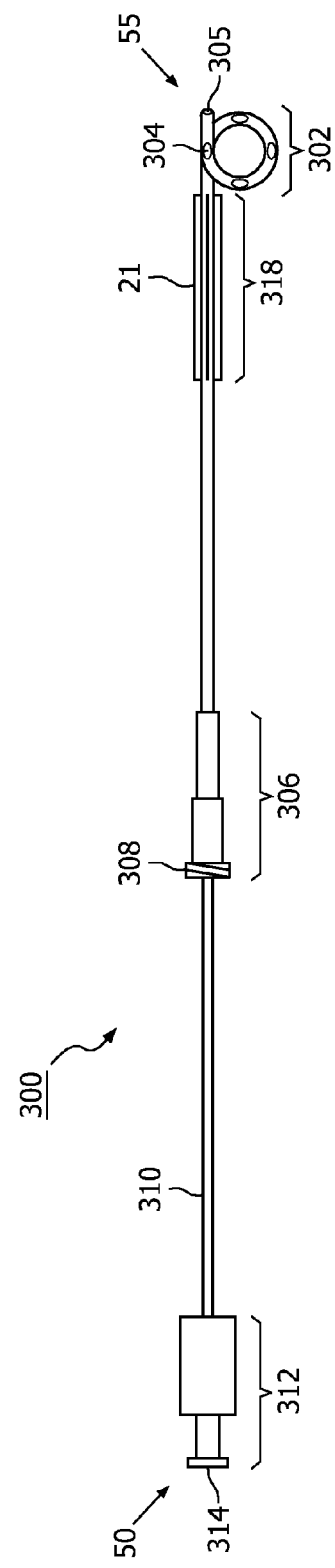
FIG. 20A
FIG. 20B

MEDICAL TUBING ASSEMBLY TO FACILITATE TUBE FIXATION

This is a U.S. national phase of PCT Application No. PCT/EP2009/063111, filed Oct. 8, 2009, which claims priority to European Application No. 08166060.7, filed Oct. 8, 2008 and U.S. Provisional Application No. 61/103,662, filed Oct. 8, 2008.

FIELD OF THE INVENTION

The invention concerns a medical tubing assembly that facilitates the secure fixation of tubing such as a brachytherapy catheter, or other type of access catheter such as for light based therapy, or drainage tube to the tissue of a subject which fixation prevents undesirable movement by the tubing.

BACKGROUND OF THE INVENTION

Medical tubing such as a catheter is employed in the art to deliver treatment to the tissue of a subject from outside the body. Medical tubing often needs to be in held in place for a long period of time e.g. days to weeks. For example, a drainage tube is commonly employed after an operation to remove a tumour, which tube prevents fluid build up from the section site. The implanted tube exits the body and is secured at the exit point by a stitch that wraps around the tubing and which hooks the adjoining skin. Another example of a medical tube is a catheter tube implanted in a subject that provides passage for a brachytherapy source wire (i.e. for example an elongated wire disposed with a radioactive tip for high dose rate or pulsed dose rate brachytherapy). The catheter needs to be held accurately in place for up to a number of weeks, so that the radiologist can provide through the tubing, brachytherapy sessions across several intervals, and to the same site of treatment. In an alternative configuration, the radiation oncologist may load the catheter tube after positioning at the described location with radioactive wires or seeds (Palladium 103, Iodine 125) both of which will remain in place for several days or weeks. Another example of a medical tube is a catheter tube implanted in a subject that provides passage for a wave guide allowing to treat an organ interstitially with light and photosensitizing agents (photodynamic therapy) or with laser light (interstitial hyperthermia with infrared light). The surgeon will typically suture the proximal end of the medical tubing as it exits the body to the surrounding skin, using a stitch that is wrapped one or more times around the tubing which hooks the adjoining skin.

Because the tubing is typically made from or coated with a friction resistive material to enable passage through the body, the stitch does not adequately grip the tubing. Since the tubing cannot be punctured by the needle, the stitch may only wrap around the exterior wall, which attachment loosens with time. As a consequence movements by the tubing in the longitudinal direction are common during wearing by the subject i.e. the tubing moves further out from or further into the body. Critically, for brachytherapy or light based applications, the position of the tubing can change over time; as a result, the precise location for delivery of brachytherapy or light can no longer be ascertained with confidence.

The prior art, therefore, demands a way to securely prohibit the medical tubing from moving in and out of the body and possibly attach medical tubing to body tissue using a suture, which allows the physician to place the stitch at one or more points along the tubing without damaging the integrity of the tubing lumen.

SUMMARY OF THE INVENTION

One embodiment of the invention is a medical tubing assembly (100) comprising:
finned medical tubing (10) formed from an elongate tubular member (20) disposed with one or more longitudinal fins (21, 21', 21"),
a collar (200), slidably mountable on the finned tubing (10), equipped with a locking means and one or more suture eyelets (250, 250'), which one or more suture eyelets (250, 250') may be optionally provided,
said locking means configured to provide a locking force against one or more of the longitudinal fins (21, 21', 21").

Another embodiment of the invention is a medical tubing assembly (100) as described above, wherein the locking means comprises one or more pins (221, 221', 221"), configured to frictionally engage or penetrate the surface of a fin (21, 21', 21").

Another embodiment of the invention is a medical tubing assembly (100) as described above, wherein the locking means comprises one or more screws, configured to frictionally engage or penetrate the surface of a fin (21, 21', 21").

Another embodiment of the invention is a medical tubing assembly (100) as described above, wherein the locking means comprises a clamp mechanism, configured to engage frictionally a surface of a fin (21, 21', 21") with at least part of an aperture (210) in the collar (200) adapted to receive slidably the finned medical tubing (10).

Another embodiment of the invention is a medical tubing assembly (100) as described above, wherein the number of fins (21, 21', 21") is one, two, three or four.

Another embodiment of the invention is a medical tubing assembly (100) as described above, wherein number of pins (221, 221', 221") or screws is equal to the number of fins, each pin (221, 221', 221") or screw configured to frictionally engage or penetrate the surface of a single fin (21, 21', 21").

Another embodiment of the invention is a medical tubing assembly (100) as described above, wherein at least one fin (21, 21', 21") projects radially from the outside surface of the elongate tubular member (20).

Another embodiment of the invention is a medical tubing assembly (100) as described above, wherein at least one pin (221, 221', 221") or screw comprises:
a pointed end (226) configured to frictionally engage or penetrate the surface of a fin (21, 21', 21"), and
head end (224) configured to receive in the case of a pin a pushing force, or in the case of a screw a rotational force, which force advances the pointed end towards a fin (21, 21', 21") to frictionally engage or penetrate its surface.

Another embodiment of the invention is a medical tubing assembly (100) as described above, wherein at least one fin (21, 21', 21") projects radially from the outside surface of the tubing increasing the maximum width of the tubing by no more than 50%.

Another embodiment of the invention is a medical tubing assembly (100) as described above, wherein the locking means is disengageable.

Another embodiment of the invention is a medical tubing assembly (100) as described above, wherein at least one longitudinal fin (21, 21', 21") extends continuously along the entire length of the elongate tubular member (20).

Another embodiment of the invention is a medical tubing assembly (100) as described above, wherein at least one fin is at least partly castellated.

Another embodiment of the invention is a medical tubing assembly (100) as described above, wherein the castellation comprises a tandem arrangement of alternating tabs (60, 60', 60", 60'") and notches (65, 65', 65", 65"'), and the tabs are adapted to facilitate entry of the tubing (10) into the subject and/or hinder withdrawal of the tubing (10) from the subject.

Another embodiment of the invention is a medical tubing assembly (100) as described above, wherein the longitudinal fins (21, 21', 21") have a continuous straight path along the length of the elongate tubular member (20).

Another embodiment of the invention is a medical tubing assembly (100) as described above, wherein the longitudinal fins (21, 21', 21") have a continuous spiral path along the length of the elongate tubular member (20).

Another embodiment of the invention is a medical tubing assembly (100) as described above, wherein the collar (20) comprises a coupling means (251).

Another embodiment of the invention is a medical tubing assembly (100) as described above, wherein said coupling means (251) is adapted to couple to an afterloader.

Another embodiment of the invention is a medical tubing assembly (100) as described above, wherein said coupling means (251) is adapted to couple to a laser emitting device.

Another embodiment of the invention is a medical tubing assembly (100) as described above, wherein said coupling means (251) comprises a Luer fitting.

Another embodiment of the invention is a medical tubing assembly (100) as described above, wherein said coupling means (251) comprises a male or female screw fitting.

Another embodiment of the invention is a catheter (300) incorporating an assembly (100) as defined above.

FIGURE LEGENDS

FIG. 1: Three dimensional view of the tubing assembly according to the invention.

Figure 2:
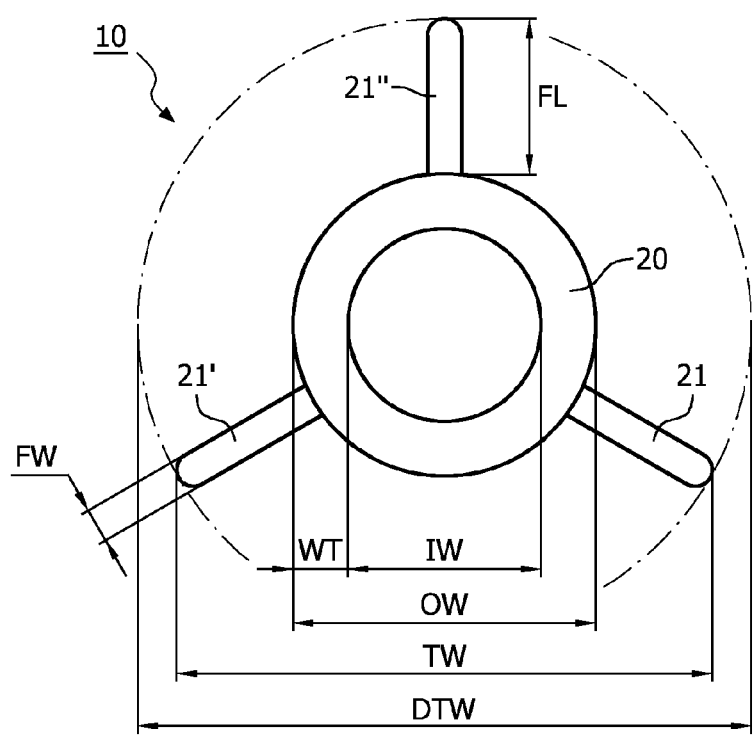

FIG. 2: Transverse cross-section through the finned tubing of the invention, with dimensions indicated.

Figure 3:
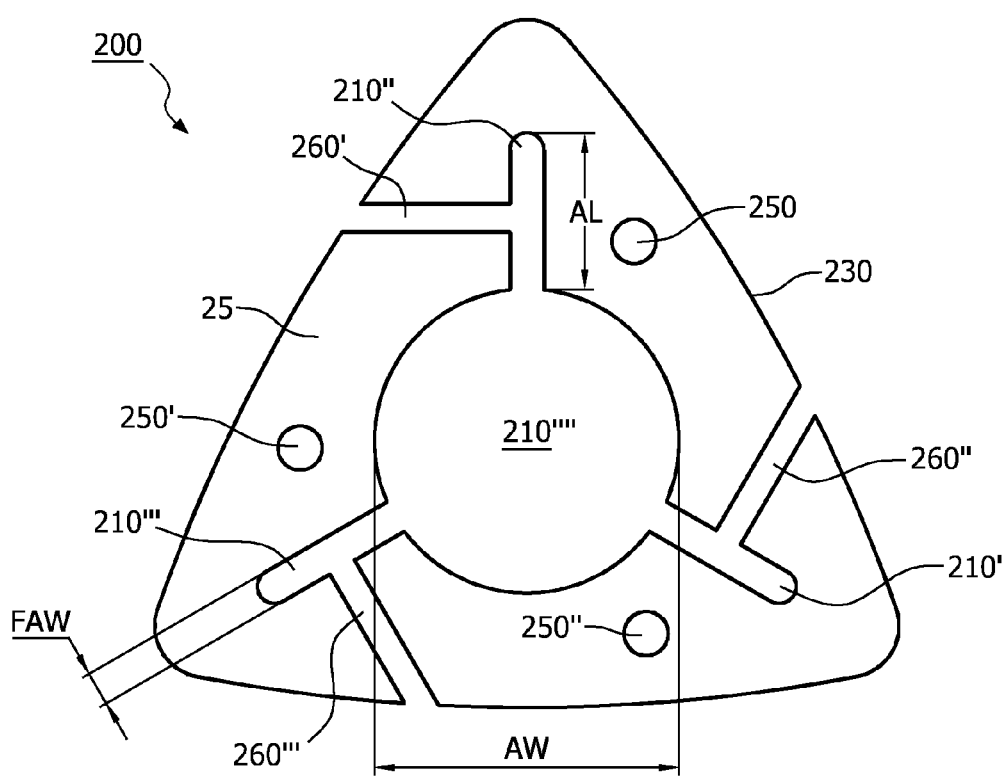

FIG. 3: Transverse cross-section through a collar of the invention.

Figure 4:
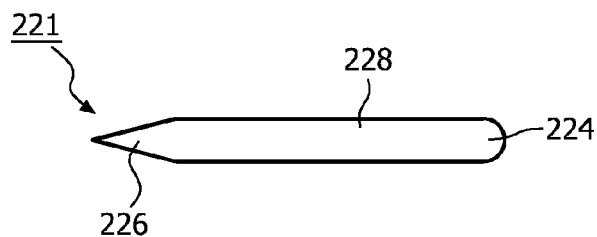

FIG. 4: Transverse cross-section through a pin of the invention.

Figure 5:
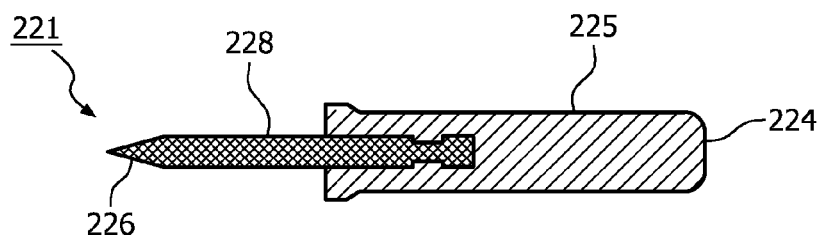

FIG. 5: Transverse cross-section through a pin of the invention disposed with a head formed from a cylindrical member.

Figure 6:
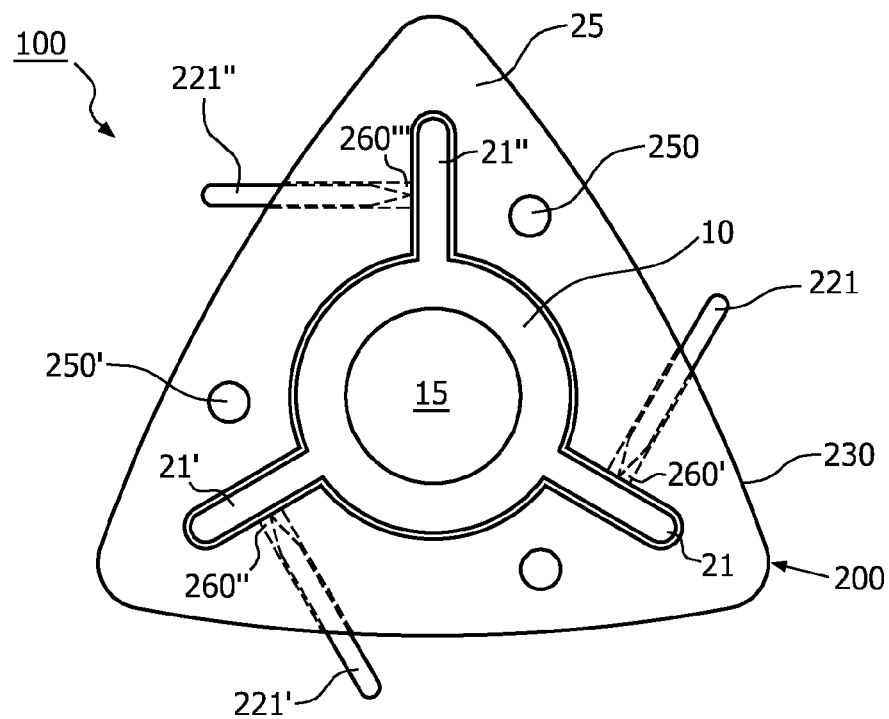

FIG. 6: Transverse cross-section through the assembly of the invention, showing a set of locking pins in an unengaged position.

Figure 7:
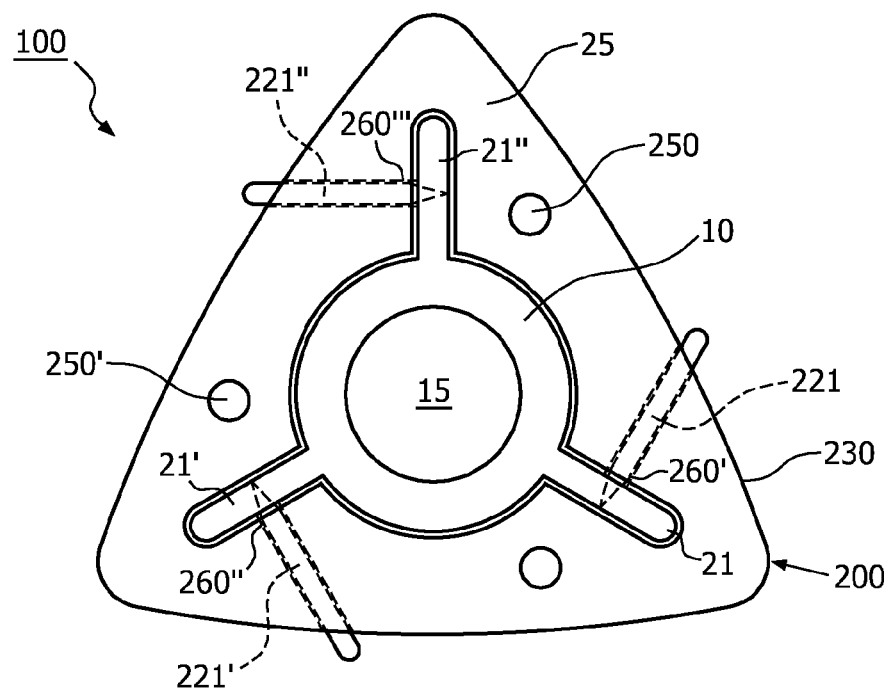

FIG. 7: Transverse cross-section through the assembly of the invention, showing a set of locking pins in an engaged position.

Figure 8:
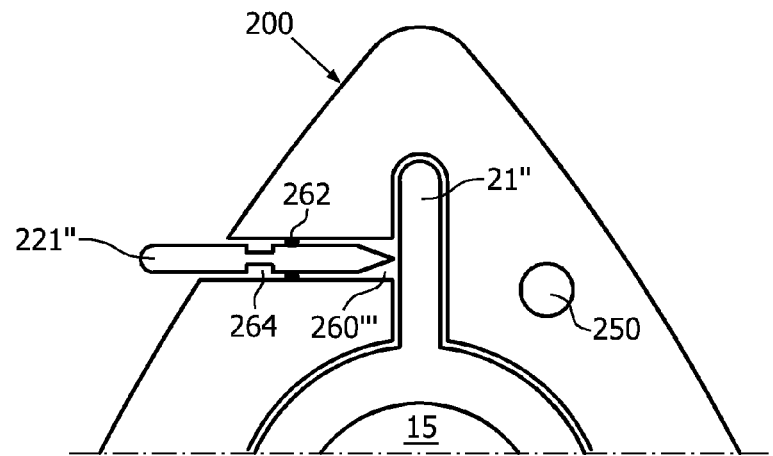

FIG. 8: Transverse cross-section through the assembly of the invention, showing a set of locking pins in an non-engaged position.

Figure 9:
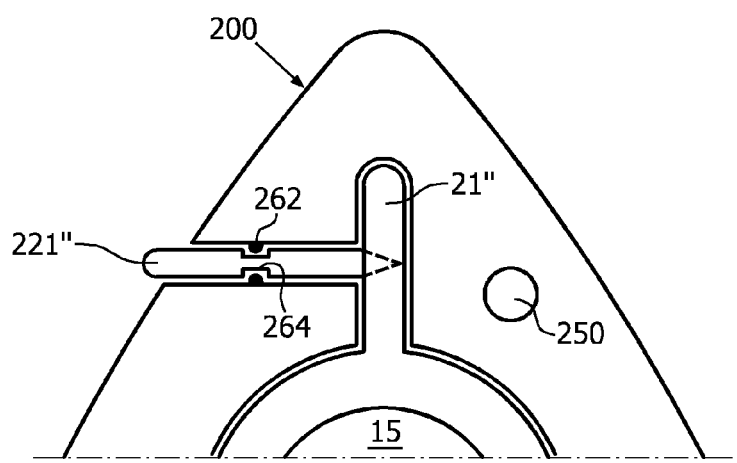

FIG. 9: Transverse cross-section through the assembly of the invention, showing a set of locking pins in an engaged position.

Figure 10:
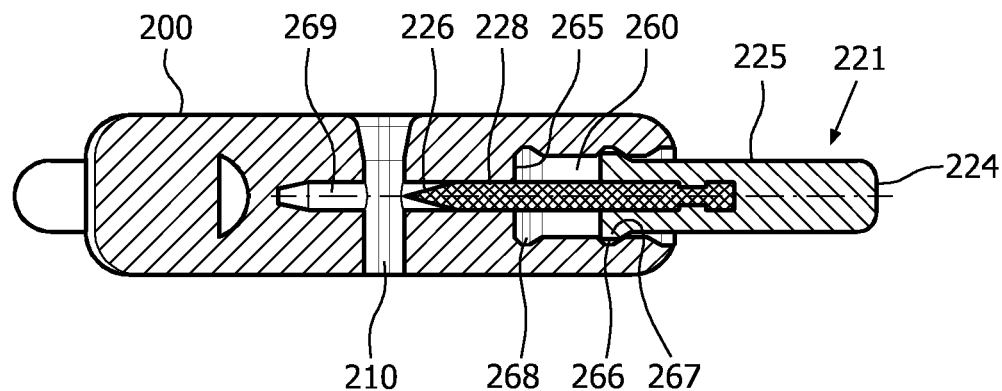

FIG. 10: Longitudinal cross-section through the assembly of the invention, showing a locking pin of the invention disposed with a protrusion, in a non-engaged position.

Figure 11:
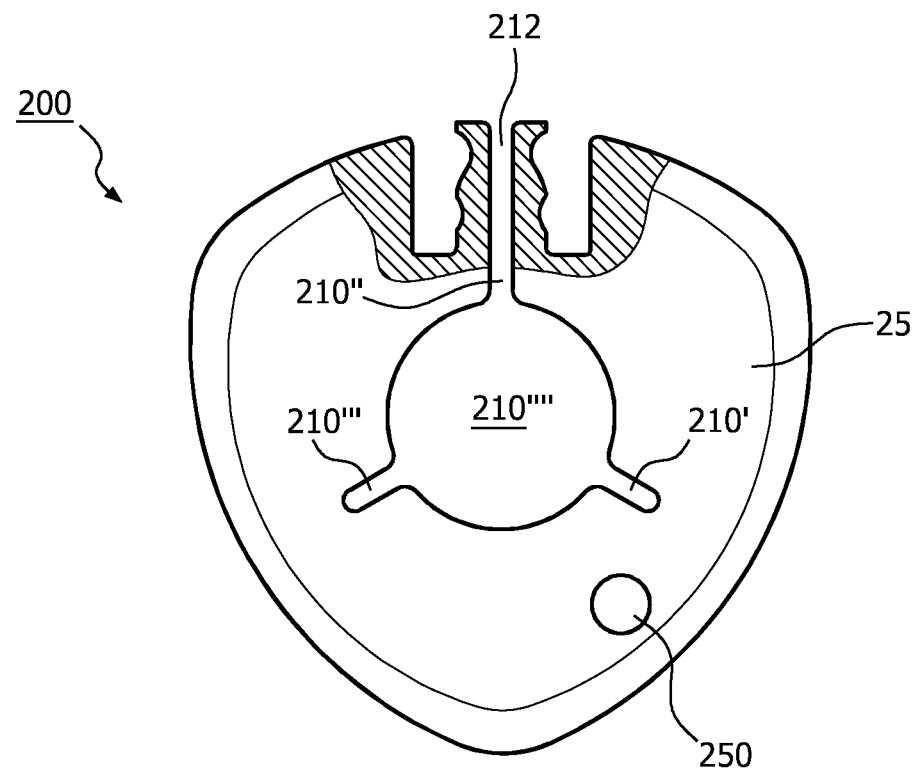

FIG. 11: Plan view of a split collar of the invention.

Figure 12:
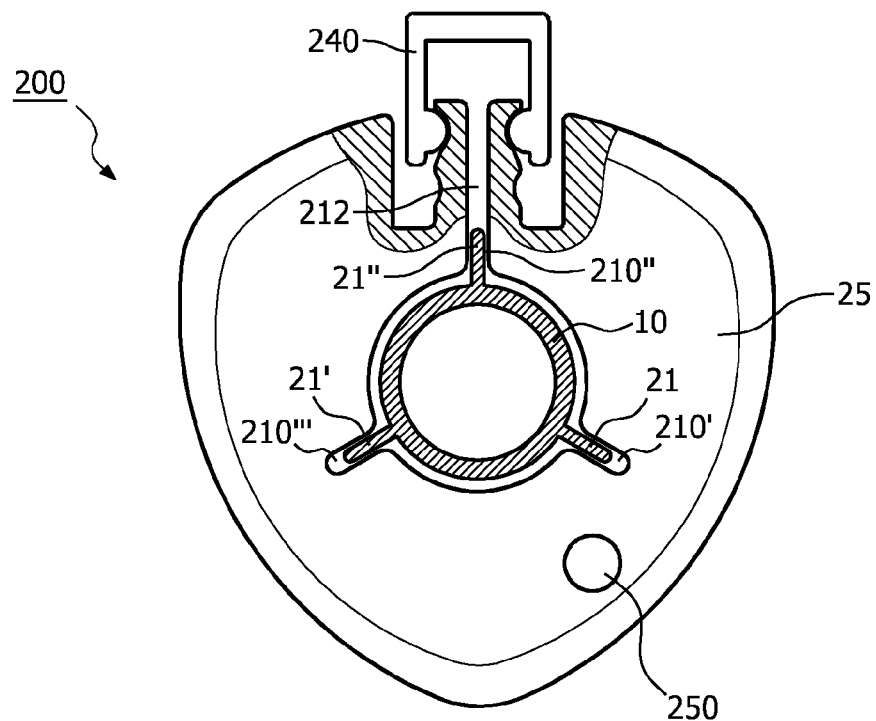

FIG. 12: Plan view of a split collar of the invention in an open (unclamped) position, disposed with finned medical tubing in the aperture.

Figure 13:
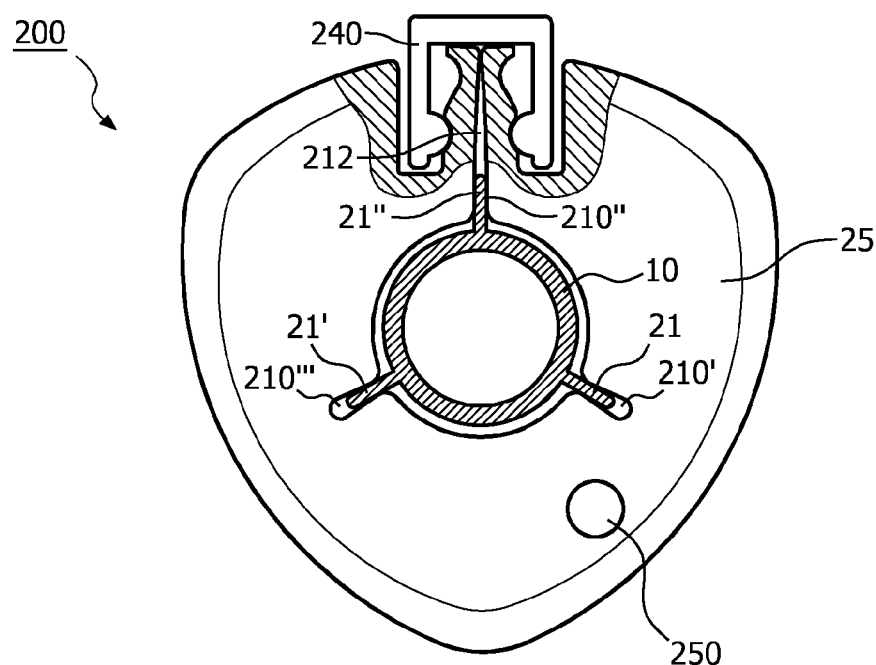

FIG. 13: Plan view of a split collar of the invention in a closed (clamped), disposed with finned medical tubing in the aperture.

Figure 14:
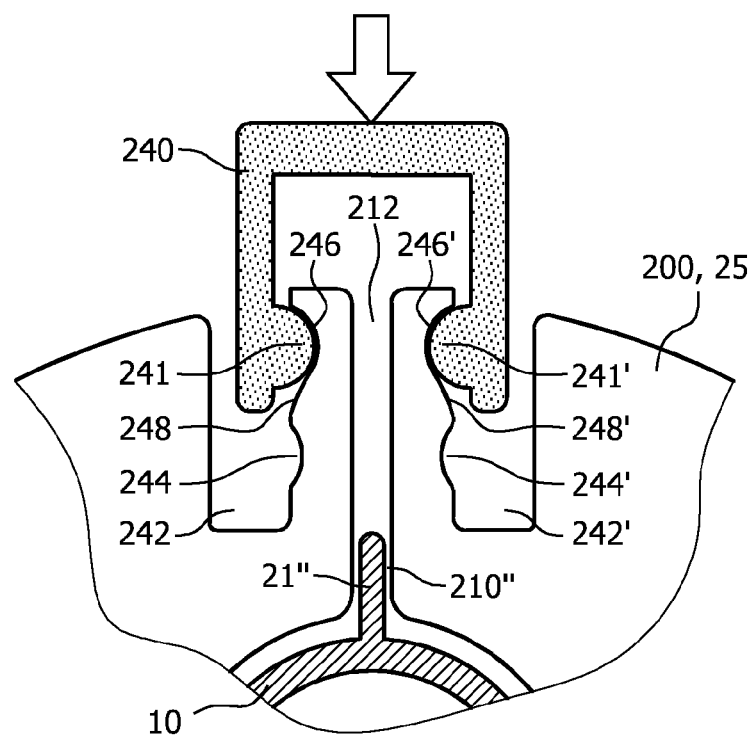

FIG. 14: Transverse cross-section through part of the assembly of the invention, showing a locking clip in a pre-engaged position.

Figure 15:
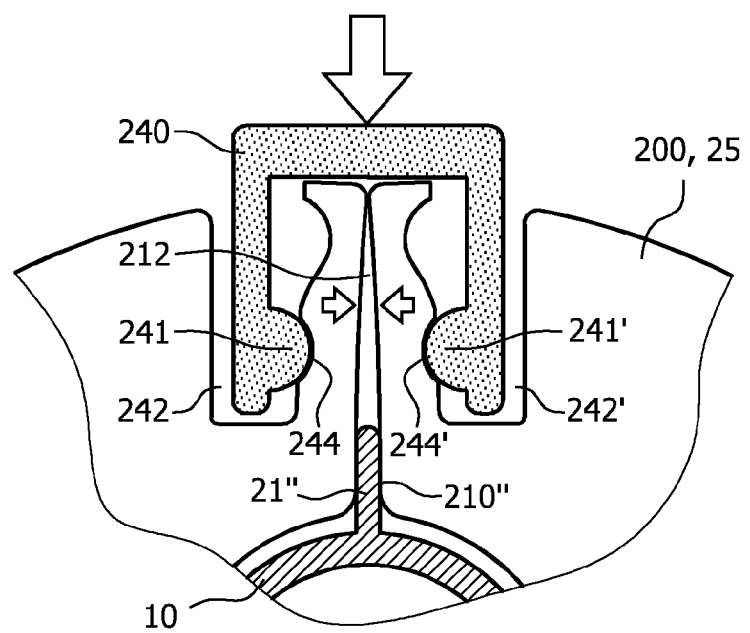

FIG. 15: Transverse cross-section through part of the assembly of the invention, showing a locking clip in an engaged position.

Figure 16:
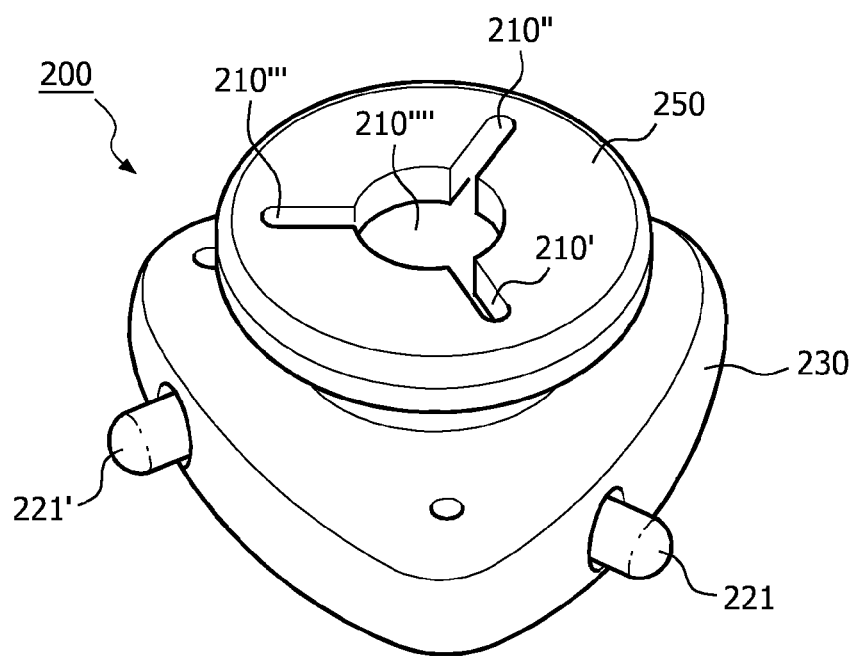

FIG. 16: Three dimensional view of a collar of the invention, provided with a coupling means.

Figure 17:
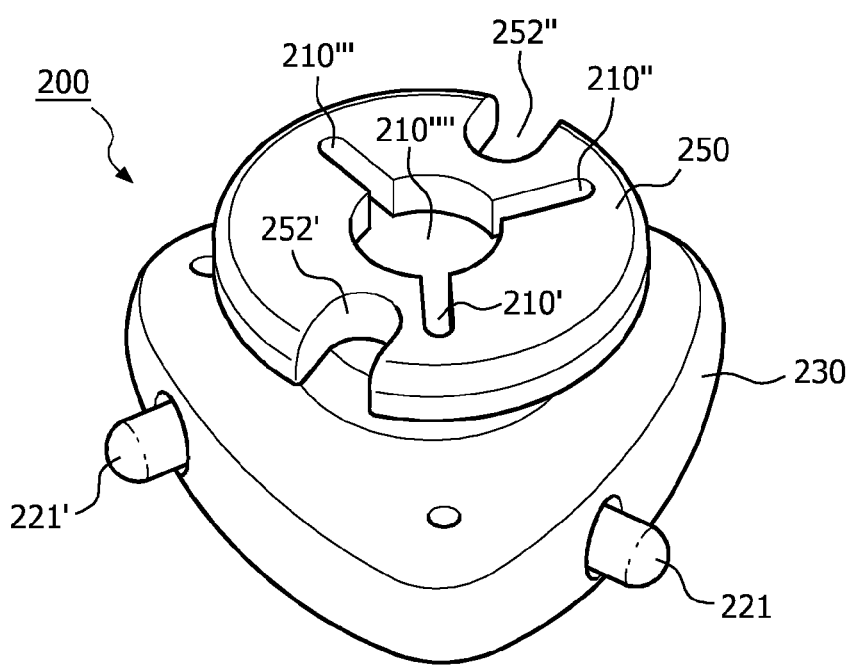

FIG. 17: Three dimensional view of a collar of the invention, provided with a coupling means disposed with locating slots.

Figure 18:
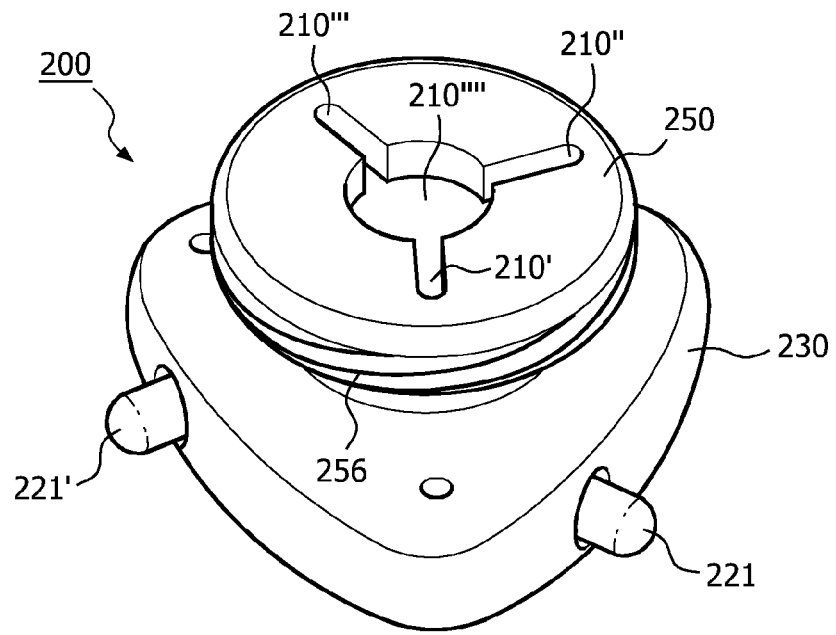

FIG. 18: Three dimensional view of a collar of the invention, provided with a coupling means disposed with a screw thread.

Figure 19:
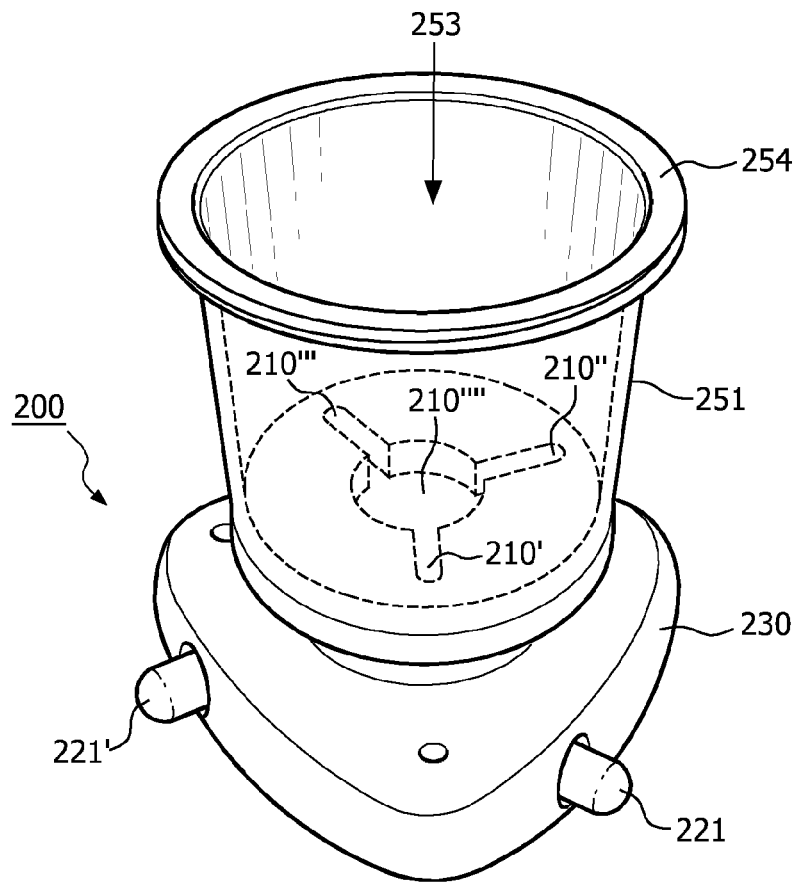

FIG. 19: Three dimensional view of a collar of the invention, provided with a coupling comprising a Luer fitting.

FIGS. 20A to 22: Three dimensional views of a pigtail catheter disposed with finned tubing of the invention, where the distal end is in a curled (FIGS. 20A & B), intermediate (FIG. 21) or straight (FIG. 22) configuration concurrent with the advancement of a stiffening stylet.

Figure 23:
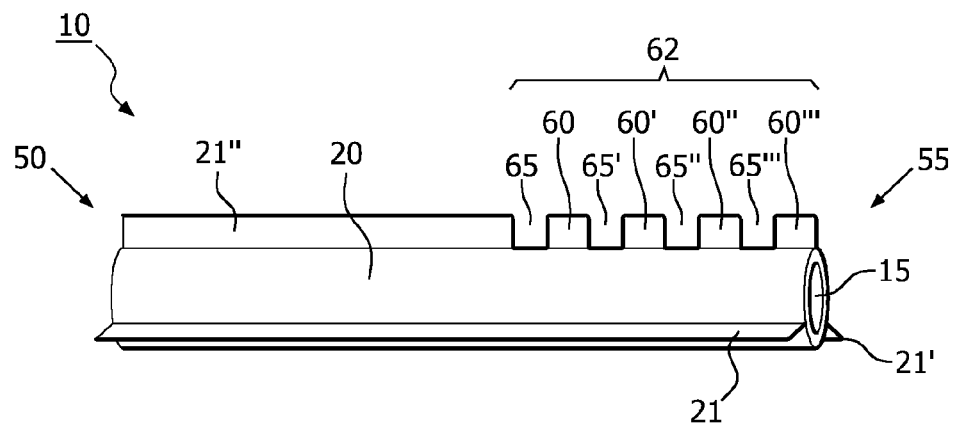

FIG. 23: Three dimensional view of a section of finned tubing, provided with rectangular castellations on one fin.

Figure 24:
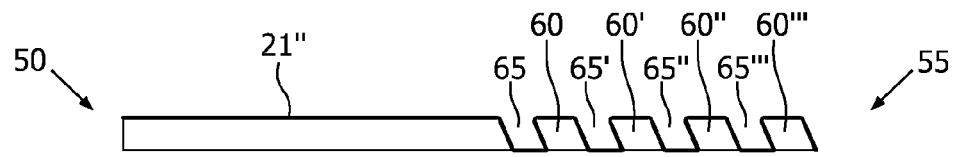

FIG. 24: Three dimensional view of a section of finned tubing, provided with sloping castellations on one fin.

Figure 25:
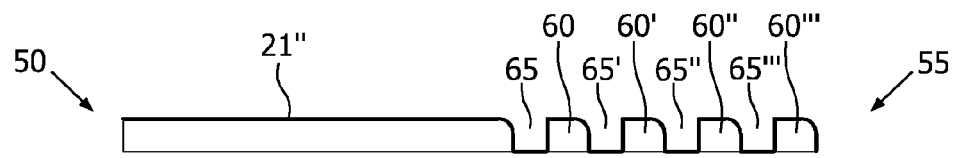

FIG. 25: Three dimensional view of a section of finned tubing, provided with rounded castellations on one fin.

Figure 26:
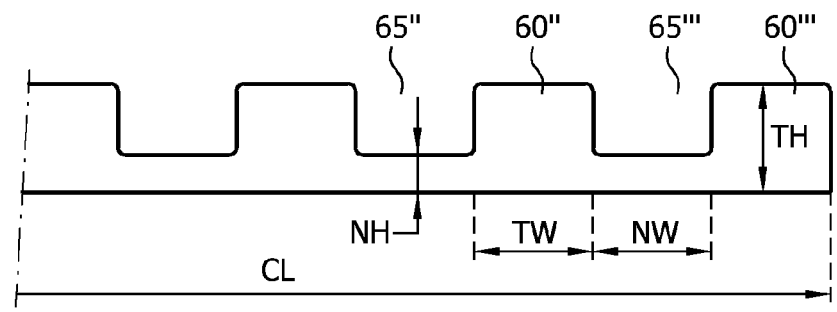

FIG. 26: View of a fin, with dimensions indicated.

DETAILED DESCRIPTION OF THE INVENTION

Unless defined otherwise, all technical and scientific terms used herein have the same meaning as is commonly understood by one of skill in the art. All publications referenced herein are incorporated by reference thereto. The articles "a" and "an" are used herein to refer to one or to more than one, i.e. to at least one of the grammatical object of the article. By way of example, "an eyelet" means one eyelet or more than one eyelet. The recitation of numerical ranges by endpoints includes all integer numbers and, where appropriate, fractions subsumed within that range (e.g. 1 to 5 can include 1, 2, 3, 4 when referring to, for example, a number of articles, and can also include 1.5, 2, 2.75 and 3.80, when referring to, for example, measurements). The recitation of end points also includes the end point values themselves (e.g. from 1.0 to 5.0 includes both 1.0 and 5.0).

With reference to FIG. 1, present invention concerns a medical tubing assembly 100 comprising:
  finned medical tubing 10 formed from an elongate tubular member 20 disposed with one or more longitudinal fins 21, 21', 21",
  a collar 200, slidably mountable on the finned tubing 10, equipped with a locking means and optionally one or more suture eyelets 250, 250',
  said locking means configured to provide a locking force against the one or more longitudinal fins 21, 21', 21".

The slidable collar may be mounted on and placed at any position along the length of the finned tubing 10, and subsequently be locked in place by the surgeon. The locking means applies a force against a fin 21, 21', 21", rather than against the tubing wall 20, as a consequence the tubing lumen 15 does not suffer from distortion or collapse which might otherwise affect the passage of fluid or of brachytherapy tubes or waveguides for light therapy. The assembly 100 does not require any special equipment to operate; it is self-contained, and requires only activation of the locking meaning, which is generally a push pin or a screw. The collar 200 provides also one or more suture eyelets 250, 250' through which medical twine can be threaded and secured to the tissue of the subject such as to the exterior skin, or to interior tissue, using a stitch.

The finned tubing 10 may be disposed with one collar, either for suturing the tubing externally or internally. Alternatively, the finned tubing may be disposed with more than one collar for suturing the tube at two or more positions internally, or at one position externally and at one or more positions internally. The collar 200 secures the finned tube 10 preventing its movement further into the entry puncture or incision. The collar 200 and stitch secure the finned tube 10 to prevent its movement further out from the puncture or incision. This can be critical when the medical tubing has been accurately placed, for example, in brachytherapy or for interstitial light based therapy, and needs to remain in situ for a number of days or weeks between treatments and without movement. Because the collar is adjustable, the assembly is suitable for any level of penetration by the tubing.

The finned medical tubing 10 is formed from an elongate tubular member 20 disposed with one or more longitudinal fins 21, 21', 21". It is disposed with a lumen 15 that extends from the proximal 50 to the distal 55 end. The finned medical tubing 10 is flexible and suitable for introduction into the subject. It is usually formed from a single, continuous length of tubing. However, it may be attached at the distal 55 and/or proximal 50 ends to other tubing of the same or different material joined end to end by heating, crimping or friction. Typically, the finned tubing 10 is formed from polyurethane, polyurethane compounds, polyimide, or other biocompatible flexible polymeric material. The tubing 10 may be coated at least on the exterior surface with an anti-microbial agent such as silver or its derivatives, chlorhexidine derivatives, heparin derivatives or any suitable anti-microbial agent that reduces the risk of infection through the point of exit from the skin.

The terms "distal" and "proximal" are used through the specification, and are terms generally understood in the field to mean towards (proximal) or away (distal) from the physician side of the apparatus. Thus, "proximal" means towards the physician side and, therefore, away from the patient side. Conversely, "distal" means towards the patient side and, therefore, away from the physician side.

With reference to FIG. 2, the total width, TW, or total diametric width, TDW, of the finned tubing is sufficiently narrow to exit through the appropriate opening with a minimum incision or skin puncture. The finned tubing is flexible. It may be flexible enough not to damage when kinked. The design of the finned tubing advantageously facilitates insertion, withdrawal and wearing, while being minimally intrusive. In wearing, the proximal end of the medical tubing protrudes from the skin, and is held in place for example, using a suture that passes through the eyelet provided on the collar. For medical applications, the total width DTW of the finned tubing will typically be 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm or 20 mm.

The elongate tubular member 20 (devoid of fins) is preferably cylindrical. As general guidance, the maximum external width of the elongate tubular member 20, or its external diameter OW, may be equal to or greater than 1 mm, 1.2 mm, 1.4 mm, 1.6 mm, 1.8 mm, 2.0 mm, 2.2 mm, 2.4 mm, 2.6 mm, 2.8 mm, 3.0 mm, 3.2 mm, 3.4 mm, 3.6 mm, 3.8 mm, 3.9 mm, 4.00 mm, 4.2 mm, 4.4 mm, 4.6 mm, 4.8 mm, 4.9 mm, 5.00 mm, 5.2 mm, 5.4 mm, 5.6 mm, 5.8 mm, 5.9 mm, 6.00 mm, 7 mm, 8 mm, 9 mm, 10 mm, 11 mm, 12 mm, 13 mm, 14 mm, 15 mm, 16 mm, 17 mm, 18 mm, or 19 mm, or a value in the range between any two of the aforementioned values, preferably between 1.6 mm and 7 mm.

The diameter of the lumen 15 of the tubing will depend on the application. For fluid delivery, it will be sufficiently wide to allow passage of fluid to the distal end, without the need to apply undue pressure at the proximal end. For the passage of wires or waveguides, as seen for example in brachytherapy or light based therapy respectively, the diameter is sufficiently larger than the diameter of the radiation source or catheter of wave guide to allow the radiation source or catheter or the wave guide to be advanced and removed from the source wire lumen without hindrance. Generally the diameter, IW, of the lumen 15 will be 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% greater than the diameter of the radiation source wire.

According to one aspect of the invention, the wall of elongate tubular member 20 has a thickness WT of 0.05 mm, 0.1 mm, 0.2 mm, 0.3 mm, 0.4 mm, 0.5 mm, 0.6 mm, 0.7 mm, 0.8 mm, 0.9 mm, 1.0 mm or a value between any two of the aforementioned values, preferably between 0.05 mm and 0.4 mm.

The tubing is preferably supplied as a length to be cut to size by the skilled practitioner before use, which length will depend on the application and location of use. For instance, in prostate cancer, the length inside the body is typically between 10 and 14 cm; for breast cancer, the length inside the body is typically between 8 and 20 cm from the tip to the collar; the tubing would be trimmed according. The tubing may be supplied as a length LC of 10 cm, 11 cm, 15 cm, 20 cm, 25 cm, 30 cm, 35 cm, 40 cm, 45 cm, 50 cm, 55 cm, 60 cm, 65 cm, 70 cm, 75 cm, 80 cm, 85 cm, 90 cm, or a value in the range between any two of the aforementioned values. Preferably, it is between 15 cm and 30 cm in length. The tubing may be supplied as a kit of two or more precut lengths of different sizes.

A fin 21, 21', 21" projects from the outside surface of the elongated tubular member 20, providing a structure for the locking means to engage with, and to prevent free lateral and free rotational movement by the locked collar. The medical tubing is disposed with one or more longitudinal fins. The number of fins may be 1, 2, 3, 4, 5, 6, 7, 8, 9 or 10, or a value in the range between any two of the aforementioned values, preferably between 1 and 4, most preferably 3. A fin may project radially from the outside surface of the tubing i.e. at a 90 degree tangent to the surface, however, other angles are envisaged within the scope of the invention, for example, at ±30, ±40, ±50, ±60, ±70, ±80 deg to the surface or at an angle in the range between any two of the aforementioned angles, preferably between 30 to 150 deg, most preferably 90 deg.

A fin 21, 21', 21" typically extends longitudinally along the entire length of the medical tubing i.e. from the tip of proximal end 50 to the tip of the distal end 55. However, at least part of the distal or proximal half may be devoid of fins and not affect functioning of the assembly. The fin 21, 21', 21" preferably extends along the length of the tubing in straight line, however, the path may deviate therefrom, for example, adopting a spiral path that causes the collar or tubing to rotate as the collar is linearly advanced. Alternatively, it may undulate, causing the collar or tubing to oscillate as the collar is linearly advanced.

A fin 21, 21', 21" that projects from the outside surface of the elongate tubular member 20 increases the total width TW of the finned tubing 10 compared with the width OW of the elongate tubular member 20 by no more than 10%, 20%, 30%, 40%, 50%, 60% or 70%, or by a value in the range between any two of the aforementioned values, preferably between 20 and 50%, most preferably by no more than 40%. The total width TW of the finned tubing refers to the maximum distance between the outer tips of two 21, 21', 21" fins.

A fin 21, 21', 21" that projects from the outside surface of the elongate tubular member 20 increases the total diametric width DTW of the finned tubing 10 compared with the width OW of the elongate tubular member 20 by no more than 10%, 20%, 30%, 40%, or 50%, or by a value in the range between any two of the aforementioned values, preferably between 10 and 30%, most preferably by no more than 20%. The diametric width DTW of the finned tubing 10 refers to the diameter of a fictive circle 30, centred at the midpoint of a transverse cross section of the finned tubing 10 that touches the outer tips of the fins 21, 21', 21".

With reference to FIG. 2, the height of a fin, FL, may be 0.2 mm, 0.5 mm, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm or 20 mm, or a value in the range between any two of the aforementioned values, preferably between 0.2 and 2 mm. Any two fins may be of equal height. Alternatively, all the fins may be of equal height. Alternatively, the majority of fins may be of equal height.

With reference to FIG. 2, the maximum width of a fin, FW, may be 0.05 mm, 0.1 mm, 0.3 mm, 0.5 mm, 0.7 mm, 1 mm, 2 mm, 3 mm, 4 mm, 5 mm, or a value in the range between any two of the aforementioned values, preferably between 0.05 mm and 2 mm.

As a general rule, the fin is made from the same material as the wall of the medical tubing. It is typically is manufactured during extrusion of the tubing and forms part of the outside wall. One embodiment of the invention relates to a method of manufacture of the assembly or tubing of the invention, comprising the step of extruding a length of finned tubing to the desired diameter.

According to one aspect of the invention, a fin 21, 21', 21" has an essentially uniform height (FL) along its longitudinal length. According to another aspect, the height (FL) of at least part of a fin 21, 21', 21" varies as a function its longitudinal length. For example, a fin 21, 21', 21" may be at least partly castellated along its longitudinal length. Thus, one embodiment of the invention is finned medical tubing 10 formed from an elongate tubular member 20 disposed with one or more longitudinal fins 21, 21', 21", as described herein, wherein at least part of a fin is castellated.

A castellated region 62 of a fin 21, 21', 21" comprises a tandem or side-by-side arrangement of alternating tabs 60, 60', 60", 60''' and notches 65, 65', 65", 65' as indicated in FIG. 23. Each and every fin 21, 21', 21" may contain a castellated region 62, alternatively, one or more (e.g. 2, 3, 4) fins may contain a castellated region 62; in FIG. 23, one fin 21" comprises a castellated region 62. The castellated region 62 may be located anywhere on a fin, for example, towards the proximal 50, distal end 55, in a mid portion. It is preferably not located at the distal 55 terminal end to prevent trauma to the region of treatment, and also it is preferably not located at the proximal 50 distal terminal end to facilitate ease of movement by the collar 200. The height (TH) of a tab 60, 60', 60", 60''' is greater that than (NH) of a notch 65, 65', 65", 65'.

The shape of a tab 60, 60', 60", 60''' may be rectangular as shown in FIG. 23, however, other shapes are envisaged. For example, the tabs may be adapted to facilitate entry of the tubing into the subject and/or hinder withdrawal of the tubing from the subject. Preferably the distal 55 edge of a tab 60, 60', 60", 60''' is adapted to facilitate entry of the tubing into the subject, while the proximal 50 edge of a tab 60, 60', 60", 60''' is adapted to hinder withdrawal of the tubing. According to one aspect of the invention, a tab 60, 60', 60", 60''' is rounded on its distal edge 55 as shown in FIG. 25. According to another aspect of the invention, the distal 55 edge of a tab 60, 60', 60", 60''' is angled (leans) towards the proximal end 50 of the tubing as shown in FIG. 24. Both aspects facilitate atraumatic entry of the tubing.

According to one aspect of the invention, the proximal 50 edge of a tab 60, 60', 60", 60''' is angled (leans) towards the proximal end 50 of the tubing as shown in FIG. 24. This aspect prevents withdrawal of the tubing without the application of force. With a castellated region of 10 cm, and tabs of 3 to 4 mm in length, a force of 3 Kg may be required to remove the assembly.

A castellated region 62 of a fin 21, 21', 21" can be defined by several parameters including the notch length, tab length, number of tabs, and the length of the region 62. Parameters of a castellated region, as indicated in FIG. 26 include the length CL of the castellated region, width TW of a tab 60", height TH of a tab 60", width NW of a notch 65', height NH of a notch 65'. As a general guidance, the following dimension may apply. The length CL of a castellated region may be equal to or greater than 2 cm, 3 cm, 5 cm, 6 cm, 8 cm, 10 cm, 12 cm or more or a value in the range between any two of the aforementioned values, preferably between 3 and 8 cm. The width TW of a tab 60", measured along its base, may be equal to or greater than 1 mm, 2 mm, 3 mm, 4 mm, 5 mm or a value in the range between any two of the aforementioned values, preferably between 2 and 4 mm. The width NW of a notch 65', measured along its base, may be equal to or greater than 1 mm, 2 mm, 3 mm, 4 mm, 5 mm or a value in the range between any two of the aforementioned values, preferably between 2 and 4 mm. The height TH of a tab 60", measured radially from the base to the tip of the tab, may be 0.2 mm, 0.5 mm, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm or 20 mm, or a value in the range between any two of the aforementioned values, preferably between 0.2 and 2 mm. The height NH of a notch 65', measured radially from the base to the tip of the notch, may be 0 mm, 0.1 mm, 0.2 mm, 0.3 mm, 0.4 mm, 0.5 mm, 3 mm, 4 mm, 5 mm, 6 mm, 7 mm, 8 mm, 9 mm, 10 mm or a value in the range between any two of the aforementioned values, preferably between 0 and 1 mm.

An at least partially castellated fin has been found to further lock the position of the medical tubing assembly in situ i.e. longitudinal withdrawal movement by the tubing is restricted. When combined with the collar 200 which prevents insertion, both unwarranted withdrawal and insertion are reduced.

A collar 200 of the invention is slidably mountable on the finned tubing 10, allowing it to move in a longitudinal direction over said tubing from the proximal 50 to distal end 55 or vice versa when the locking means is not engaged. The collar 200 has a body 25, with a generally flattened form, and an aperture 210 running between the flattened surfaces that receives the finned tubing 10. The collar 200 is equipped with an engagable locking means that in the engaged position prevents longitudinal movement of the collar relative to the finned tubing 10 and in the non-engaged position permits longitudinal movement of the collar relative to the finned tubing 10. The body 25 of the collar 200 is preferably adapted to prevent movement by the collar 200 past the incision typically by having a flattened shape that extends at least partly over the opening of the incision when the collar is for suturing to the skin. Being so configured, the collar may not be taken into the incision. When the collar is for suturing internally, it is not necessarily a requirement that it should be adapted to prevent movement by the collar 200 past the incision. The collar 200 may be made from any bio-compatible material that has the requisite properties i.e. has a low coefficient of friction and has sufficient strength to support a suture. Suitable materials include PEEK, polypropylene, polyoxypropylene (Delrin 500P™) and others.

The aperture 210 may have a profile (transverse cross section) that matches the profile (transverse cross section) of the finned tubing, and is slightly larger than finned tubing profile to allow movement by the collar 200 without substantial hindrance. The profile of the collar aperture 210 may be larger than that of the finned tubing by 1%, 5%, 10%, 15%, 20%, 25%, 30%, 35%, or a value in the range between any two of the aforementioned values, said values representing a difference in area.

With reference to FIG. 3, which depicts a transverse cross-section of a collar 200, the aperture 210 comprises a circular component 210'''' that reciprocates the circumference of elongate tubing member 20, and three slot components 210', 210'', 210''' that reciprocate each of the fins 21, 21', 21''. The circular component 210'''' may have a diameter AW that is equal to or no more than 1%, 2%, 3%, 4%, 5%, 6%, 7%, 8%, 9%, 10%, 15%, or 20% larger than the diameter OW of the tubular member 20, or a value in the range between any two of the aforementioned values, preferably between 1 and 10% larger. A slot component 210', 210'', 210''' may have a width FAW that is equal to or no more than 1%, 2%, 3%, 4%, 5%, 6%, 7%, 8%, 9%, 10%, 15%, or 20% larger than the width FW of a fin of the tubular member 20, or a value in the range between any two of the aforementioned values, preferably between 1 and 10% larger. A slot component 210', 210'', 210''' may have a length AL that is equal to or no more than 1%, 2%, 3%, 4%, 5%, 6%, 7%, 8%, 9%, 10%, 15%, or 20% larger than the length FL of a fin of the tubular member 20, or a value in the range between any two of the aforementioned values, preferably between 1 and 10% larger.

The locking means (mechanism) provides a locking force against a fin, meaning that it provides force against the fin 21, either frictional, penetrative or otherwise that prevents the collar 200 from moving longitudinally. In the locked position, the locking means is engaged, and the collar 200 may not move longitudinally along the finned tubing 10; in the non-locked position, the locking means is not engaged, and the collar 200 may move slidably longitudinally along the finned tubing 10. The locking means may be any, for example, a pin, screw or clamp as elaborated below.

The locking means most preferably takes the form of a pushable pin 221, 221', 221'' or rotatable screw, configured for advancement to and for frictional or penetrative contact with a single tubing fin 21, 21', 21''. Where the locking means comprises a pin, (FIGS. 4 and 5), the pin 221, 221', 221'' typically comprises a shaft 228 that is an elongated member, preferably cylindrical, disposed with a head 224 at one end and a tip 226 at the other end. While the present invention has been illustrated principally with a pin locking mechanism (e.g. FIG. 1), it must be understood the invention is not limited thereto, and the locking mechanism may be any, which includes those described below.

The head 224 presents a surface for the application of force in the longitudinal direction of the pin, for example using a finger, thumb, set of pliers, screwdriver or other suitable object, to move the pin towards the aperture, and into the locked position. The head 224 may be formed from the terminal end of the shaft 228 as shown in FIG. 4. Alternatively, the head 224 may be formed from a member 225 attached to the shaft 228, which member provides a greater surface area for the application of force. As shown in FIG. 5. the member 225 may comprise an essentially cylindrical form, having a diameter greater than that of the pin shaft 228.

The tip 226 is most preferably pointed, though other shapes are envisaged including rounded, rivet shaped, or flat. The non-pointed tip may be provided with a friction-enhancing coating such an abrasive diamond coating. The pin or screw is dimensioned to sit in a passage 260', 260'', 260''' in the body 25 of the collar 200.

The body 25 of the collar 200 preferably comprises a linear passage 260', 260'', 260''' (FIG. 3) that runs from the peripheral surface 230 of the collar toward the aperture 210, particularly towards the slot component 210', 210'', 210'''. The number of passages may be equal to the number of fins 21, 21', 21''. The passage 260', 260'', 260''' is configured to retain the pin or screw, and to prevent movement thereof without the application of external force. The passage 260', 260'', 260''' is also configured to guide pin or screw in a straight line towards the aperture 210, particularly the slot component 210', 210'', 210'''. The passage 260', 260'', 260''' preferably lies such that its central axis is normal to the fin 21, 21', 21'' or slot component 210', 210'', 210'''. The passage preferably has an essentially cylindrical shape. It may adopt the profile (longitudinal cross section) of the pin 221 or screw. The passage 260', 260'', 260''' may extend from the peripheral surface 230 of the collar 200, past the slot component 210', 210'', 210''' and into the inner body of the collar 200 where it forms a well 269 (see FIG. 10) that can accommodate the tip 226 of the pin 221 or screw in cases when it spears the fin 21, 21', 21'' in the locked position.

Various configurations of pin 221 are within the scope of the invention. For instance, with reference to FIGS. 8 and 9, the shaft of the pin 221'' may be disposed with a circumferential groove 264 configured to engage with a complementary protrusion 262 in the passage 260''' when the pin 221'' is advanced to the locked position (FIG. 9). Linear movement of the protrusion 262 into the groove 264 provides feedback (e.g. sound or vibration) indicating the pin 221'' has advanced sufficiently. While FIGS. 8 and 9 depict a pin 221 disposed with a groove and the protrusion disposed in the passage 260''', the inverse configuration (not shown) is within the scope of the invention, i.e. the groove may be disposed in the passage and the protrusion disposed on the pin.

In an alternative configuration depicted in FIG. 10, the head 224 of the pin 221 is formed from a cylindrical member 225 that is disposed with a protrusion 267, and the passage 260 is disposed with a first groove 266, which accommodates said protrusion 267 when the pin 221 is housed in the passage 260. The protrusion 267 is preferably an annular or partly annular ring. The groove 266 may be annular or partly annular, and is preferably a notch in the wall passage 260. The first groove 266 and protrusion 267 are configured such that they disengagably support the pin 221 in the non-locked position, the tip 226 of the pin 221 not contacting the fin 21, 21', 21'' when the protrusion 267 is engaged in the first groove 266. Applying a force to the head 224 of the pin 221 disengages the protrusion 267 from the first groove 266 allowing the tip 226 of the pin 221 to advance towards the slot component 210 and to contact the fin 21, 21', 21'' in the locked position. The passage 260 may be disposed with a limit stop 265 that restricts the linear distance by which the pin 221 may advance; as shown in FIG. 10, the limit stop 265 contacts the cylindrical member 225 that forms the head of the pin 221 when the pin 221 is in the locked position. A second groove 268 in the passage 260 may abut the limit stop 265, which second groove 268 is configured to engage the protrusion 267 of the pin 221 when the pin is in the locked position. The second groove 268 prevents the pin 221 from retreating out from the passage 260.

FIG. 6 depicts a transverse cross-section of a collar 200 mounted on a finned tubing 10 of the invention. The locking means is shown as is a set of slidably mounted pins 221, 221', 221'' each within a passage 260', 260'', 260''' in the body 25 of the collar 200. In the non-locked position, there is no or insufficient frictional or penetrative contact between the pins 221, 221', 221'' the fins 21, 21', 21'' of the tubing 10 to prevent linear advancement of the tubing 10 through the collar 200. FIG. 7 also depicts a transverse cross-section of a collar 200 mounted on a finned tubing 10 of the invention where the pins 221, 221', 221" are in the locked position i.e. after the pins 221, 221', 221" have been advanced towards the fins 21, 21', 21" of the tubing 10. Each pin 221, 221', 221" penetrates and pierces each fin 21, 21', 21" of the tubing 10 thereby fixing the position of the collar 200 relative to the finned tubing 10. The lumen 15 of the finned tubing 10 remains unbreeched.

The pin 221, 221', 221", may be made from single material or combination of materials that have the requisite compression strength i.e. does not deform upon the application of force in the longitudinal direction, for example, stainless steel, titanium, nitenol, PEEK, bakelite or polycarbonate. The member 225, where present, that forms pin head 224, may be made from any material that has the requisite compression strength i.e. does not deform upon the application of force in the longitudinal direction, for example, stainless steel, titanium, nitenol, PEEK, bakelite or polycarbonate.

In an alternative embodiment, the locking means is a screw (not illustrated) configured to advance linearly towards the single tubing fin 21, 21', 21" by the application of rotational force. The screw comprises a threaded shaft, disposed with a head at one end and a tip at the other end. The shaft may be tapered or non-tapered. The diameter of the head may be larger than that of the tip. The head is configured (e.g. slotted, Philips, Pozidriv, Hex (Allen), Double hex) for coupling with a tool for the application of rotational force that drives the screw in the longitudinal direction towards the aperture, preferably the slotted component. The screw tip is most preferably pointed, though other shapes are envisaged included rounded, rivet shaped, or flat. The non-pointed tip may be provided with a friction-enhancing coating such an abrasive diamond coating. The screw is dimensioned to sit in a passage 260', 260", 260''' in the body 25 of the collar 200, which passage may be at least partially reciprocally threaded to engage with the screw thread. The screw may be made from any material that has the requisite compression strength i.e. does not deform upon the application of rotational force, for example, stainless steel, titanium, nitinol or polycarbonate.

In an alternative embodiment, the locking means comprises a clamp mechanism configured to engage frictionally at least part of the aperture 210 in the collar 200 with a surface of a fin 21, 21', 21", preferably the side walls. More in particular, the clamp mechanism is configured to frictionally engage a slot component 210', 210", 210''' of an aperture 210, with a surface of a fin 21, 21', 21". By doing so, the side walls of a fin 21, 21', 21" are clamped against the collar 200. The fin is clamped by the application of pressure either side of the fin, applied through the walls of a slot component 210', 210", 210'''. When the walls of a slot component 210', 210", 210''' are compressed towards the fin, the collar is clamped and slidably locked. When the walls are released, the collar is also released and is slidable again relative to the tubing 10.

FIG. 11 shows a particular embodiment of a collar 200 disposed with a clamp mechanism. In this embodiment the collar 200 is split by virtue of a closable gap 212 extending outwards from one of the slots component 210', 210", 210''' towards the periphery of the collar 200. When the gap 212 is open and tubing 10 present in the aperture as shown in FIG. 12, no pressure is applied via the slot component 210" to the corresponding fin 21"; the tubing can slide relative to the collar 200. When the gap 212 is closed as shown in FIG. 13, pressure is applied via the walls of the slot component 210" to the side walls of the corresponding fin 21"; the tubing is clamped, and its position slidably locked relative to the collar 200. A slidable clip 240 may be employed to control the opening and closure of the gap 212 which clip flanks the gap 212; when the clip 240 is in an upper (pre-engaged) position (FIG. 14) the gap 212 is open and the tubing can slide relative to the collar 200. When the clip 240 is in a lower (engaged) position, i.e. pushed into the collar (FIG. 15) the gap 212 is closed, the slot component 210" presses against the fin 21", and the tubing 10 is clamped relative to the collar 200.

The clip 240 preferably has a U-shaped profile, i.e. has two legs connected by a cross-piece. Each of the two legs is disposed with an inward pointing rounded protrusion 241, 241' positioned towards the open ends of the legs, each protrusion configured to releasably engage with a reciprocating upper recess 246, 246' in the collar 200, each recess present in a pair of slots 242, 242' that flanks the gap 212. When the clip 240 protrusions 241, 241' are seated in the upper recess 246, 246', the clip is in a pre-engaged position (FIG. 14) and the gap 212 is open. Each slot 242, 242' is further equipped with a lower reciprocating recess 246, 246' which lower recesses are adapted to received the protrusions 241, 241' when the clip 240 is advanced further into the slots 242, 242'. The lower reciprocating recess 244, 244' are positioned at a greater distance from the gap 212 compared with the upper recess 246, 246', with the result that the movement by the clip into the lower recess 244, 244' (FIG. 15) forces narrowing of the gap 212, and there is a concomitant clamping of the fin 21" to the slot component 210". To facilitate movement by the clip 240, the path 248, 248' between the upper recess 246, 246' and the lower recess 244, 244', may be gradual.

The clip 240, may be made from single material or combination of materials that have the requisite compression and tensile strength i.e. does not deform upon the downward application and when seated in the lower recess, for example, stainless steel, titanium, nitenol or polycarbonate.

The collar 200 is optionally provided with one or more suture eyelets 250, 250'. A suture eyelet 250, 250' has an opening suitable for the passage of a needle and thread. It has the requisite strength to support the collar while sutured to the tissue. Typically it will be provided towards the periphery of the collar.

The number of collars 200 mounted on the finned tubing 10 may be 1, 2, 3, 4, 5, 6, 7, 8, 9, 10 or more, or a number in the range between any two of the aforementioned numbers. When the finned tubing 10 is disposed with one collar 200, it may be used for suturing the tubing externally i.e. to the skin, or internally i.e. to internal tissue such as adipose, muscle, connective tissue. When the finned tubing 10 is disposed with more than one collar 200, the collars 200 may be used to suture the tube at two or more positions internally, or at two or more positions externally, or at one position externally and at one or more positions internally. Advantageously, internal and external sutured collars provide improved anchoring, and prevent, for instance, movement of the external collar into the body due to a sudden pulling motion.

Besides optionally providing a structure to immobilize and/or to suture medical tubing to the skin, the collar 200, suitably adapted, may further provide a coupling means 251 for attachment of another element such as another tubing or a device. After the implanted medical tubing 10 has been shortened above the collar, it leaves the proximal end 50 of the tubing terminating with an open end. By virtue of a coupling means 251 that extends from the collar, the open end can be directly attached to, for example, an extension tubing to assist with drainage or aspiration of an internal cavity. This coupling means 251 may alternatively be used to introduce a brachytherapy catheter connected to an afterloader for the delivery of brachytherapy or a wave guide connected to a laser emitting instrument. One embodiment of the invention is an assembly 100 as described herein, wherein the collar 200 is further provided with a coupling means 251. The coupling means 251 preferably extends from the proximal end 50 of the collar 200. The coupling means preferably provides a water impermeable connection to a reciprocating coupling means. According to one embodiment of the invention, the coupling means 251 comprises a circular flange as shown, for instance, in FIG. 16. According to one embodiment of the invention, the coupling means 251 comprises a circular flange disposed with a pair of radial locating notches 252', 252" as shown, for instance, in FIG. 17. According to one embodiment of the invention, the coupling means 251 comprises screw thread, as shown, for instance, in FIG. 18. While FIG. 18 shows a male type thread on the exterior circumferential edge of the flange, it may, alternatively by a female thread extending into the circular component 210"" of the aperture. According to another embodiment of the invention, the coupling means 251 comprises a Luer fitting, disposed on the proximal 50 side. The Luer fitting can be any e.g. male or female, threaded or non-threaded. Illustrated in FIG. 19 is a Luer fitting configured to engage a male non-threaded syringe-type fitting with its internal conical passage 253, or a female threaded Luer connection with its outer threaded rim 254. The Luer fitting facilitates connection to standard equipment, such as to medical tubing, a valve or a drainage cap.

One embodiment of the invention is an inline fitting having at one end a self-tapping threaded male connector adapted for rotational insertion into the lumen 15 of the finned tubing 10, and at the other end, a connector for external tubing. When screwed into position, the fitting sealably connects the proximal end of the lumen 15 of the finned tubing 10 with the lumen of an external tubing. The fitting may be straight or angled (e.g. 90 deg). The fitting is particularly suited for connection to the proximal 50 end of finned tubing 10, when it has been truncated flush with the proximal side of the collar 200.

The finned medical tubing 10 may be incorporated into a catheter of the art. That is to say, the outer shaft of a lumened catheter of the art may be at least partially disposed with fins along its longitudinal length. Commonly there is a need to maintain a catheter position in situ, for example, during the course of treatment which lasts several days, which the present tubing provides. Examples of catheters incorporating the finned medical tubing 10 of the invention include a drainage catheter and a brachytherapy catheter. The finned medical tubing 10 may be provided towards the proximal 50 end, in a central region, or towards the distal 55 end of the catheter, or may be disposed essentially along the entire longitudinal length of the catheter, depending on the application. The finned medical tubing 10 may be incorporated using any technique including extrusion, heating, crimping, gluing or friction. The catheter may further be provided with the collar 200 of the invention, preferably mounted.

Figure 21:
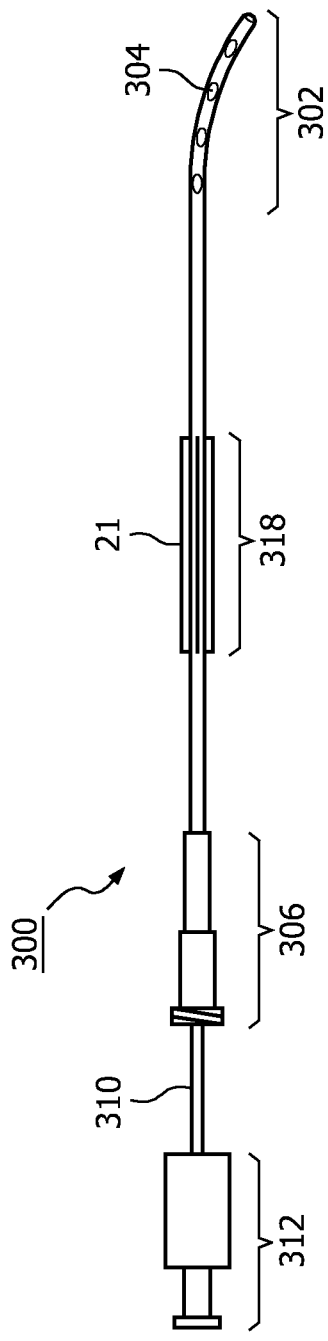
Figure 22:
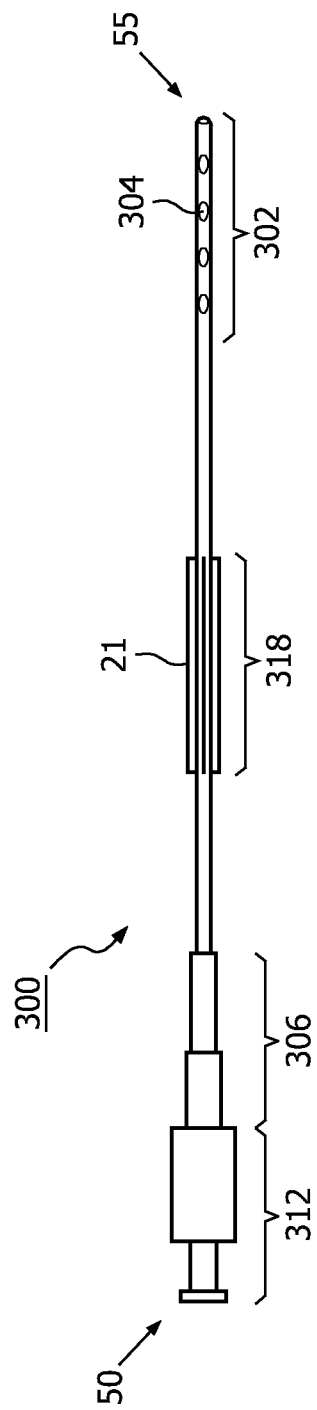

One embodiment of the invention is a pigtail drainage catheter incorporating a finned medical tubing 10 of the invention. A pigtail drainage catheter is known in the art, and is characterised by a perforated curled distal end, adapted to straighten or linearise by the advancement of a stiffening stylet through a drainage lumen connecting the perforations with the port on the proximal end. An example of a pigtail catheter 300 is given in FIGS. 20A, 20B, 21 and 22. FIGS. 20A and B show the pigtail drainage catheter 300 in its native state, comprising a curled distal 55 end region 302 disposed with perforations 304 for the passage of fluid; it also has a distal terminal port 305. The proximal 50 end of the catheter 300 contains a handle region 306 that terminates in a male screw connector 308 surrounding an open proximal port (not shown). A drainage lumen (not shown) connects the proximal port with the distal terminal port 305 and perforations 304. The proximal port is adapted to receive a stiffening stylet 310 having a distal end 55 tip for advancement into the drainage lumen, and a proximal 50 end handle region 312. The handle region 312 of the stylet 310 is provided at the proximal 50 end with a Luer connection, and at the distal 55 end with a female threaded opening (not shown) adapted to engage with the male thread of the catheter handle region 306. In FIG. 20A, the pigtail catheter incorporates a finned medical tubing of the invention in a region 318 disposed towards a central portion of the catheter longitudinal shaft. In FIG. 20B, the pigtail catheter incorporates a finned medical tubing of the invention in a region 318 towards the distal end 55 of the catheter. One of the three fins 21 is labelled in FIGS. 20A to 22. FIGS. 21 and 22 illustrate a sequential uncurling of the catheter shown in FIG. 20B. When the stiffening stylet 310 is partially advanced into the drainage lumen, the curled distal 55 end region 302 is partially straightened (FIG. 21). When fully advanced, the curled distal 55 end region 302 is fully straightened (FIG. 22); the male screw connector 308 of the catheter handle region 306 may engage with the reciprocating female threaded opening at the distal end of the handle region 312 of the stylet. While the finned region 318 is shown towards the distal end 55 (FIGS. 20B to 22), or central part (FIG. 20A), it may equally be disposed towards the proximal end 50 of the pigtail catheter (not shown). Although not shown, the pigtail catheter may further be provided with the collar 200 of the invention, preferably mounted over the finned region 318.

The present invention also includes the assembly defined here for use as a catheter. In particular, it includes the catheter for use as a drainage catheter, as a brachytherapy catheter, or as a wave guide catheter. The present invention also includes the use of an assembly as defined herein as a catheter, in particular as a drainage catheter, as a brachytherapy catheter, or as a wave guide catheter. The present invention also includes the assembly as defined herein for use in medical treatment, in particular for use in the treatment of a tumour by brachytherapy.

The invention claimed is:

1. A medical tubing assembly (100) comprising:
   finned medical tubing (10) formed from an elongate tubular member (20) disposed with one or more longitudinal fins (21, 21', 21"),
   a collar (200), slidably mountable on the finned tubing (10), equipped with a locking means and optionally one or more suture eyelets (250, 250'),
   said locking means configured to provide a locking force against one or more of the longitudinal fins (21, 21', 21").

2. Assembly according to claim 1, wherein the number of fins (21, 21', 21") is one, two, three or four.

3. Assembly according to claim 1, wherein at least one fin (21, 21', 21") projects radially from the outside surface of the elongate tubular member (20).

4. Assembly according to claim 1, wherein the locking means comprises one or more pins (22, 221', 221"), configured to frictionally engage or penetrate the surface of a fin (21, 21', 21").

5. Assembly according to claim 1, wherein the locking means comprises one or more screws, configured to frictionally engage or penetrate the surface of a fin (21, 21', 21").

6. Assembly according to claim 4, wherein number of pins (221, 221', 221") or screws is equal to the number of fins, each pin (221, 221', 221") or screw configured to frictionally engage or penetrate the surface of a single fin (21, 21', 21").

7. Assembly according to claim 4, wherein at least one pin (221, 221', 221") or screw comprises:

a pointed end (226) configured to frictionally engage or penetrate the surface of a fin (21, 21', 21"), and head end (224) configured to receive in the case of a pin a pushing force, or in the case of a screw a rotational force, which force advances the pointed end towards a fin (21, 21', 21") to frictionally engage or penetrate its surface.

8. Assembly according to claim 1, wherein the locking means comprises a clamp mechanism, configured to engage frictionally a surface of a fin (21, 21', 21") with at least part of an aperture (210) in the collar (200) adapted to receive slidably the firmed medical tubing (10).

9. Assembly according to claim 1, wherein at least one fin (21, 21', 21") projects radially from the outside surface of the tubing increasing the maximum width of the tubing by no more than 50%.

10. Assembly according to claim 1, wherein the locking means is disengageable.

11. Assembly according to claim 1, wherein at least one longitudinal fin (21, 21', 21") extends continuously along the entire length of the elongate tubular member (20).

12. Assembly according to claim 1, wherein at least one fin is at least partly castellated.

13. Assembly according to claim 12, wherein the castellation comprises a tandem arrangement of alternating tabs (60, 60', 60", 60'") and notches (65, 65', 65", 65'"), and the tabs are adapted to facilitate entry of the tubing (10) into the subject and/or hinder withdrawal of the tubing (10) from the subject.

14. Assembly according to claim 1, wherein the collar (20) comprises a coupling means (251).

15. Assembly according to claim 14, wherein said coupling means (251) is adapted to couple to an afterloader.

16. Assembly according to claim 14, wherein said coupling means (251) is adapted to couple to a laser emitting device.

17. Assembly according to claim 14, wherein said coupling means (251) comprises a Luer fitting.

18. Assembly according to claim 14, wherein said coupling means (251) comprises a male or female screw fitting.

19. A catheter (300) incorporating an assembly (100) as defined in claim 1.

* * * * *